US006380167B1

(12) United States Patent
Braude

(10) Patent No.: US 6,380,167 B1
(45) Date of Patent: Apr. 30, 2002

(54) METHODS FOR ANTI-TUMOR THERAPY

(75) Inventor: Irwin Braude, Seattle, WA (US)

(73) Assignee: PrimeCyte, Inc., North Seattle, WA (US)

(*) Notice: Subject to any disclaimer, the term of this patent is extended or adjusted under 35 U.S.C. 154(b) by 0 days.

(21) Appl. No.: 09/502,544

(22) Filed: Feb. 10, 2000

Related U.S. Application Data
(60) Provisional application No. 60/119,943, filed on Feb. 12, 1999.

(51) Int. Cl.$^7$ ............................................. A61K 31/705
(52) U.S. Cl. ....................................................... 514/26
(58) Field of Search ......................................... 514/26

(56) References Cited

U.S. PATENT DOCUMENTS

| | | | |
|---|---|---|---|
| 3,514,441 A | | 5/1970 | Satoh et al. |
| 3,531,462 A | | 9/1970 | Satoh et al. |
| 3,843,628 A | | 10/1974 | Minato |
| 3,857,832 A | | 12/1974 | Hartenstein et al. |
| 3,939,156 A | | 2/1976 | Albrecht et al. |
| 3,949,074 A | | 4/1976 | Eberlein et al. |
| 4,001,402 A | | 1/1977 | Albrecht et al. |
| 5,545,623 A | | 8/1996 | Matsumori |
| 5,872,103 A | * | 2/1999 | Belletti .................. 514/26 |
| 5,891,855 A | | 4/1999 | Florkiewicz |
| 6,071,885 A | * | 6/2000 | Florkiewicz .......... 514/26 |

FOREIGN PATENT DOCUMENTS

| WO | WO 97/28808 | 8/1997 |
|---|---|---|

OTHER PUBLICATIONS

Al–Said et al., (1988) *Phytochemistry*, vol. 27, No. 10, pp. 3245–3250.
Antman K., et al., (1993) "Anintergroup Phase Ill Randomized Study of Doxorubicin and Dacarbazine With or Without Ifosfamide and Mesna in Advanced Soft Tissue and Bone Sarcomas." *J Clin Onc*, vol. 11, pp. 127~1285.
Baek et al., (1994) *Planta Med.*, vol. 60, No. 1, pp. 26–29.
Bailar et al., (1997) *N. Engl. J. Med.*, vol. 336, pp. 1569–1574.
Borden EC, et al., (1987) "Randomized Comparison of Three Adriamycin Regimens for Metastic Soft Tissue Sarcomas" *J Clin Onc* vol. 5, pp. 840–850.
Boring CC, et al., (1991) *CancerSstatistics CA*, vol. 41, pp. 19–39.
Doskotch et al., (1972) *J. Pharmaceutical Sciences*, vol., 61, No. 4, pp. 570–573.
*The Merck Index,* pp. 117 (1996) Merck & Co., Inc. Publishers, 12$^{th}$ edition.
Omura GA, et al., (1983) "A Randomized Study of Adriamycin With and Without Dimethytriazenoimidazole Carboxamide in Advance Uterine Sarcoma" *Cancer,* vol. 52, pp. 62~632.

Ozols RF., et al., (1999) "Randomized Phase III Study of Cisplatin (CIS/Paclitaxel (PAC) Versus Carboplatin ((CARBO)/PAC in Optimal Stage III Epthelial Ovarian Cancer (OC): A Gynecologic Onocology Group Trial. (Proc. ASCO Abstract 1373)" *J Clin Oncol,* vol. 18, pp. 356a.
Repeke et al., (1995) *Anti–Cancer Drug Design*, vol. 10, pp. 177–187.
Shiratori, (1967) *GANN,* vol. 58, pp. 521–528.
Stenkvist B., et al., (1999) "Is digitalis a Therapy for Breast Carcinoma:" *Oncol Rep,* vol. 6, pp. 493–496.
Stenkvist et al., (1982) "Cardiac Glycosides and Breast Cancer, Revisited" *The Lancet,* p. 484.
Stenkvist B., et al., (1980) "Evidence of a Modifying Influence of Heart Glucosides on the Development of Breast Cancer." *Analytical and Quantitative Cytology,* vol. 2, pp. 49–54.
Stenkvist et al., (1979) "Cardiac Glycosides and Breast Cancer" *The Lancet,* vol. 1, p. 563.
Yang JC, et al., (1993) "Sarcomas of Soft Tissues, in: Cancer:", *Principles & Practice of Oncoiogy,* Fourth Edition., pp. 1436–1488.
Zhang et al., (1996) *Chinese Medical Journal,* vol. 109, No. 6, pp. 478–481.
Umehara, et al., (1995) Studies on Differentiation Inducers.V.$^{1)}$ Steroid Glycosides from Periplocae Radicis Cortex. Chem Pharm. Bull. 43:(9) pp. 1565–1568.
Edmonson JH, et al., (1993) "Randomized Comparison of Doxorubicin Alone Versus Ifosfamide Plus Doxorubicin or Mitomycin, Doxorubicin and Cisplatin Against Advanced Soft Tissue Sarcomas." *J Clin Onc,* vol. 11, pp. 1269–1275.
Friedman GD, et al., (1984) "Digitalis and Breast Cancer." *Lancet,* vol. 2, p. 875.
Garg R, et al., (1997) "The Effect of Digoxin on Mortality and Morbidity Inpatients With Heart Failure." *N Engl J Med,* vol. 336, pp. 525–533.
Gheorghiade M, et al., (1997) "Digitalis Investigation Group (DIG) Trial: A Stimulus for Further Research." *Am Heart J,* vol. 134, pp. 3–12,.
Gil et al., (1995) *J. Natural Products,* vol. 58, pp. 848–856.
Goldin AG, et al., (1984) "Digitalis and Cancer." *Lancet,* vol. 1, p. 1134.
Goodman and Gilman, (1996) "The Pharmacological Basis of Therapeutics", 9$^{th}$ edition, Hardman and Limbard eds, p. 810.

(List continued on next page.)

*Primary Examiner*—Jerome D. Goldberg
(74) *Attorney, Agent, or Firm*—McDonnell Boehnen Hulbert & Berghoff

(57) ABSTRACT

The present invention provides novel methods, pharmaceutical compositions, and articles of manufacture for treating tumors that involve administering an effective amount of digitoxin, or a pharmaceutical salt thereof, wherein the tumor is selected from the group consisting of mesotheliomas, sarcomas, carcinomas, stromal cell, and germ cell tumors.

4 Claims, No Drawings

OTHER PUBLICATIONS

Goodman and Gilman, (1996) "The Pharmacological Basis of Therapeutics", 9th edition, Hardman and Limbard eds., p. 1736.

Horowitz et al.,(1988) *Journal of Clinical Oncology,* vol. 6, No. 2, pp. 308–314.

Hyun et al., (1995) *Planta Med.,* vol. 61, pp. 294–295.

Inada A, et al., (1993) "Anti–tumor Promoting Activities of Natural Products. II Inhibitory Effects of Digitoxin on Two–Stage Carcinogenesis of Mouse Skin Tumors and Mouse Pulmonary Tumors." *Biol. Pharm. Bull,* vol. 16, pp. 930–931.

Kaneda et al., (1992) *Planta Med.* vol. 58, pp. 429–431.

Kitinaka et al., (1996) *Chem. Phar. Bull.,* vol. 44, No. 3, pp. 615–617.

Kupchan et al., (1964) *J. Med. Chem.,* vol. 17, p. 803.

Kupchan et al., (1964) *Science,* vol. 146, p. 1685.

Landis S., et al., (1999) "Cancer Statistics." *Cancer J Clin.,* vol. 49, pp. 8–24.

LeWinn, (1979) *The Lancet,* pp. 1196–1197.

McGuire WP., et al., (1996) "Cyclophosphamide and Cis–platin Compared with Paclitaxel and Cisplatin in Patients With Stage III and Stage IV Ovaraian Cancer." *N Engl J Med* vol. 334, pp. 1–6.

Raben RH and Wassermann O: "A New, Alkylating Deriva–tive of Cassaine" Arzneim. Forsch., vol. 24, No. 6, (1974), pp. 956–957.

Tobin, T., et al., "Interaction of Ouabain and Cassaine with Na++K+–ATPase in Pre–Screens for Anti–Cancer Agents" Anti–Cancer Drug Design, GB, Basingstoke, vol. 10 (1995), pp. 177–187.

\* cited by examiner

METHODS FOR ANTI-TUMOR THERAPY

RELATED APPLICATION

This application claims priority to U.S. Provisional Patent Application Ser. No. 60/119,943, filed Feb. 12, 1999, and is related to the subject matter in co-pending U.S. patent application, Ser. No. to be assigned, filed Feb. 10, 2000 (Case number 99,005-B)

BACKGROUND OF THE INVENTION

Approximately twenty percent of deaths from all causes in the United States are cancer-related. Although chemotherapy is a principal means of cancer treatment, the rate at which effective new drugs have become available for use in cancer chemotherapy has not increased (Horowitz et al., Journal of Clinical Oncology, Vol. 6, No. 2, pp. 308–314 (1988)). Despite many years of promising new therapies, cancer remains a major cause of morbidity and mortality. (Bailar et al., N. Engl. J. Med. 336:1569–1574, 1997) Accordingly, there is a substantial need for new drugs which are effective in inhibiting the growth of tumors.

Cardiac glycosides are potent and highly selective inhibitors of the active transport of $Na^+$ and $K^+$ across cell membranes and act by binding to the alpha subunit of the $Na^+ K^+$-ATPase. The affinity of the alpha subunit for cardiac glycosides varies among species and among the three known mammalian alpha subunit isoforms, each of which is encoded by a separate gene. (Goodman and Gilman, "The Pharmacological Basis of Therapeutics, $9^{th}$ edition, Hardman and Limbird eds, p. 810 (1996)). These compounds share a steroid nucleus containing an unsaturated lactone ring at the C17 position and one or more glycosidic residues at C3, and occur naturally in many plants and several toad species, usually acting as venoms or toxins that serve as protection against predators. (Id).

Cardiac glycosides have been used extensively as therapeutics in the treatment of heart failure. (Goodman and Gilman, "The Pharmacological Basis of Therapeutics, $9^{th}$ edition, Hardman and Limbird eds, p. 810 (1996)). Digitoxin has been the most widely used cardiac glycoside, with a therapeutic plasma concentration of greater than 10 ng/ml (approximately 13 nM). However, digitoxin is toxic at concentrations of above 35 ng/ml (approximately 46 nM) (Id. at 1736). Thus, the therapeutic window for digitoxin in the treatment of heart failure is quite narrow.

Cardiac glycosides have also been shown to inhibit cell proliferation in a wide variety of cell lines in vitro. (See for example Kaneda et al., Planta Med. 58:429–431 (1992), Gil et al., J. Natural Products 58:848–856 (1995), Kitinaka et al., Chem. Pharm. Bull. 44(3):615–617 (1996), Baek et al., Planta Med. 60(1):26–29 (1994), Zhang et al., Chinese Medical Journal 109(6):478–481 (1996), Shiratori, GANN 58:521–528 (1967), Doskotch et al., J. Pharmaceutical Sciences 61(4):570–573 (1972), Kupchan et al., J. Med. Chem 17:803 (1964), Kupchan et al., Science 146:1685 (1964), Hyun et al., Planta Med. 61:294–295 (1995), Al-Said et al., Phytochemistry 27(10):3245–3250 (1988)). This in vitro activity was routinely shown to be non-selective, as the proliferation of almost all tumor cell lines were inhibited, and occurred at similar (generally toxic) doses across the different cell lines. Studies have also suggested that cardiac glycosides can be used to inhibit the export of leaderless proteins from cells (U.S. Pat. No. 5,891,855), as well as inhibiting inflammatory cytokine secretion (U.S. Pat. No. 5,545,623), but only at toxic doses.

Based on these in vitro findings, numerous cardiac glycosides have been screened for their ability to inhibit in vivo tumor growth. (See, for example, LeWinn, The Lancet Jun. 2, 1979, p. 1196–1197; Stenkvist et al., The Lancet Mar. 10, 1979 p. 563; Stenkvist et al., The Lancet Feb. 25, 1982, p. 484.) However, the results of these in vivo studies have uniformly proven disappointing, as any therapeutic activity was found only at toxic doses. (Repke et al., Anti-Cancer Drug Design 10:177–187 (1995)). Based on all of these studies, the use of cardiac glycosides as effective anti-neoplastic agents would be entirely unexpected.

SUMMARY OF THE INVENTION

The present invention is based on the entirely unexpected finding that digitoxin can act as an effective anti-neoplastic agent. In one aspect, the present invention provides novel methods for treating tumors that involve administering an effective amount of digitoxin, or a pharmaceutical salt thereof, to a patient in need of such treatment, wherein the tumor is selected from the group consisting of mesotheliomas, sarcomas, carcinomas, stromal cell, and germ cell tumors.

In further aspects, the present invention provides pharmaceutical compositions comprising an effective amount for treating tumors of digitoxin, or a pharmaceutical salt thereof, in a suitable carrier, and an article of manufacture comprising packaging material and the above pharmaceutical composition.

DETAILED DESCRIPTION OF THE INVENTION

All references cited herein are incorporated by reference in their entirety.

As used herein, the term "effective amount" means a dosage sufficient to produce adesired result. The desired result can be subjective or objective improvement in the recipient of the dosage, a decrease in tumor size, time to progression of disease, and/or survival.

As used herein the term "mesothelioma" is used to refer to a neoplasm derived from the cells lining the pleura, pericardium, or peritoneum, including but not limited to lung mesotheliomas.

As used herein the term "sarcoma" refers to tumors of mesenchymal origin, including but not limited to leiomyosarcomas, malignant fibrous histiocytoma, Ewing sarcoma, fibrosarcomas, chondrosarcomas, osteosarcomas, liposarcomas, rhabdomyo-sarcomas, hemangiocytomas, and myxosarcomas.

As used herein the term "carcinoma" is used to refer to a neoplasm derived from epithelial cells.

As used herein the term "ovarian carcinoma" refers to neoplasms derived from ovarian cells of epithelial origin, including but not limited to ovarian papillary serous cystadenoma, ovarian endometroid carcinoma, mucinous, clear cell and Brenner epithelial tumors;

As used herein the term "lung carcinoma" refers to neoplasms derived from lung cells including but not limited to squamous cell carcinomas, adenocarcinomas, oat cell carcinomas, carcinoid tumors, giant cell tumors, mucoepidermoid tumors, and adenoidcystic carcinomas.

As used herein the term "kidney carcinoma" refers to neoplasms derived from kidney cells including but not limited to renal cell carcinomas, Wilm's tumor, and hamartoma.

As used herein the term "germ cell tumors" refers to neoplasms including, but not limited to, dysgerminomas, and yolk sac tumors.

As used herein the term "stromal cell tumors" refers to neoplasms including, but not limited to granulosa cell, thecoma, and Sertoli-Leydig tumors.

In one aspect, the present invention provides new methods treating tumors that involve administering an effective amount of digitoxin, or a pharmaceutical salt thereof, to a patient in need of such treatment, wherein the tumor is selected from the group consisting of mesotheliomas, sarcomas, carcinomas, stromal cell, and germ cell tumors.

Digitoxin can be prepared by any of the methods known in the literature. Non-limiting examples of these methods include those disclosed in U.S. Pat. Nos. 3,514,441; 3,531,462; 3,843,628; 3,857,832; 3,939,156; 3,949,074; and 4,001,402, all references incorporated by reference herein in their entirety. Alternatively, digitoxin is commercially available (for example, Sigma Chemical Co., St. Louis, Mo.).

As disclosed herein, digitoxin and pharmaceutical compositions including digitoxin are useful in treating mesotheliomas, sarcomas, carcinomas, stromal cell and germ cell tumors. Examples of specific tumor types that the compounds may be used to treat include, but are not limited to solid tumors including ovarian papillary serous cystadenoma and ovarian endometroid carcinoma, lung mesothelioma, malignant fibrous histiocytoma, leiomyosarcoma, Ewing sarcoma, hemangiocytomas. Other ovarian tumors, such as mucinous, clear cell and Brenner epithelial tumors; germ cell tumors including dysgerminomas and yolk sac tumors; and stromal cell tumors including granulosa cell, thecoma, and Sertoli-Leydig tumors, are also treatable. Other sarcomas treatable with the compounds of the invention include fibrosarcomas, chondrosarcomas, osteosarcomas, liposarcomas, rhabdomyosarcomas, and myxosarcomas.

Preferred examples of carcinomas that may be treated with digitoxin include ovarian, kidney, and lung carcinomas.

In another preferred embodiment, digitoxin is used to treat ovarian papillary serous cystadenomas, ovarian endometroid carcinomas, mesotheliomas, malignant fibrous histiocytomas (a sarcoma), leiomyosarcomas, hemangiocytomas, liposarcomas, and Ewing sarcomas.

The digitoxin can be administered individually or in combination with other anti-tumor agents, usually in the form of a pharmaceutical composition. Such compositions are prepared in a manner well known in the pharmaceutical art and comprise at least one active compound. Accordingly, the present invention also includes pharmaceutical compositions comprising as active ingredient digitoxin associated with a pharmaceutically acceptable carrier, and the invention further comprises the method of treating susceptible neoplasms using the compositions containing digitoxin.

The digitoxin can be administered as the sole active pharmaceutical agent, or they can be used in combination with one or more other anti-tumor agents. When administered as a combination, the digitoxin and other anti-tumor agents can be formulated as separate compositions that are given at the same time or different times, or they can be given as a single composition.

The digitoxin may be made up in a solid form (including granules, powders or suppositories) or in a liquid form (e.g., solutions, suspensions, or emulsions). The digitoxin may be applied in a variety of solutions and may be subjected to conventional pharmaceutical operations such as sterilization and/or may contain conventional adjuvants, such as preservatives, stabilizers, wetting agents, emulsifiers, buffers etc.

For administration, digitoxin is ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the compounds of this invention may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

Pharmaceutical compositions containing digitoxin are administered to an individual having a tumor. In therapeutic applications, compositions are administered to a human patient in an amount sufficient to cause regression of the tumor, or at least partially arrest tumorigenesis and metastasis. Amounts effective for this use depend on factors including, but not limited to, the nature of the compound (specific activity, etc.), the manner of administration, the stage and severity of the cancer, the weight and general state of health of the patient, and the judgment of the prescribing physician. The digitoxin is effective over a wide dosage range. For example, dosages per day will normally fall within the range of about 1 $\mu$g/kg to about 0.8 mg/kg of body weight. In the treatment of adult humans, the range of about 1 $\mu$g/kg to about 0.1 mg/kg of body weight, in single or divided doses, is preferred, while 5 $\mu$g/kg to about 30 $\mu$g/kg is most preferred. However, it will be understood that the amount of the compound actually administered will be determined by a physician, in the light of the relevant circumstances including the condition to be treated, the choice of compound to be administered, the chosen route of administration, the age, weight, and response of the individual patient, disorders affecting the heart, and other specific organ dysfunction, and therefore the above dosage ranges are not intended to limit the scope of the invention in any way.

The digitoxin may be administered by any suitable route, including orally, parentally, by inhalation or rectally in dosage unit formulations containing conventional pharmaceutically acceptable carriers, adjuvants, and vehicles, including liposomes. The term parenteral as used herein includes, subcutaneous, intravenous, intraarterial, intramuscular, intrasternal, intratendinous, intraspinal, intracranial, intrathoracic, infusion techniques, intracavity, or intraperitoneally. In a preferred embodiment, the compounds of the invention are administered orally or parentally.

The instant invention may be embodied in other forms or carried out in other ways without departing from the spirit or essential characteristics thereof. The present disclosure and enumerated examples are therefore to be considered as in all respects illustrative and not restrictive, the scope of the invention being indicated by the appended claims, and all equivalency are intended to be embraced therein. One of ordinary skill in the art would be able to recognize equivalent embodiments of the instant invention, and be able to practice such embodiments using the teaching of the instant disclosure and only routine experimentation.

Example 1

Tissue Processing

Excess tissue specimens obtained from a variety of organs and tissues such as colon, lung, kidney, stomach, and buttocks were obtained freshly at the time of surgery and samples were sent for pathological testing. For diagnosis and grading of tissue samples (ie: prior to processing), hematoxylin and eosin stained tissue sections were examined by a pathologist. If the diagnosis and grading of the tissue concurred with the determination made by the surgical pathologist that provided the tissue, then the tissue was used in the screen. If there was no agreement, then two additional pathologists served as referees. If no consensus was reached, then the tissue was discarded.

The remaining tissue was used to prepare cell suspensions. The tissue was initially treated enzymatically via standard methods until only undigested material remained. The resulting cell suspension was further purified via isokinetic density centrifugation.

Additional normal cells were removed from the cell suspension by negative immunoselection with a combination of monoclonal antibodies linked to magnetic beads (Dynal) that were used according to the manufacturers' instructions. The remaining cells were placed into appropriate medium, frozen down in one ml aliquots, and stored until use.

Example 2

General Screen/Bioassay Procedures

After tissue processing, the relative purity of the resulting cell suspension was determined by cytological examination after pap staining. Only those cell preparations greater than 80% tumor cells were used for testing of candidate compounds. If there was any doubt about the percentage of tumor cells in the cell preparation, additional pathologists served as referees to make a determination.

Cell preparations that passed histological and cytological examination for diagnosis, grading, and cell purity were thawed at 37° C. and resuspended in tissue culture medium designed to maintain the cells during the incubation period. The live and dead cells were counted and the cells were diluted in culture medium to $4.0 \times 10^4$ live cells/ml for tumor cells and $1.32 \times 10^5$ live cells/ml for normal cells.

The cells were added to microtiter plates and incubated at 37° C. for one hour with 10 μm of digitoxin that was added at 1/10 the volume of the cell suspension. Alamer Blue (Accumed International, Westlake Ohio) was then added to the cells at 1/10 the volume of the well, and the cells were further incubated at 37° C. for various times. Alamer Blue dye measures cellular re-dox reactions (ie: cellular respiration) whereby a spectral shift occurs upon reduction of the dye. (Excitation 530 nm; emission 590 nm)

The kinetics of cellular re-dox reactions were subsequently measured at various times, for example at 3 hours, 3 days, and 5 days post-dye addition. These measurements, in comparison with control cells (untreated with compound) and media controls (test wells without cells) provide the percent inhibition of cellular respiration as a result of digitoxin treatment, as well as $IC_{50}$ determinations.

The Alamer Blue data were subsequently confirmed by microscopic observation, and by the use of calcein AM (Molecular Probes, Eugene Oreg.), a cell permeant esterase substrate that measures both esterase activity and cell membrane activity. If the cell is alive, the dye is converted into a fluorogenic substrate by intracellular esterases and is retained by the cell (excitation 485 nm; emission 530 nm). If the cells are dead, the calcein AM rapidly leaks from the cells, and is not converted into a fluorogenic substrate. Thus, the assay is useful for cytotoxicity testing.

Example 3

Anti-Tumor Pilot Screen

In a blinded fashion, approximately 10,000 compounds were tested at a rate of 1,000–4,000 compounds per run set against colon, lung, and sarcoma tumors. The anti-tumor screen utilized was composed of three tiers as follows. In screen 1, patient tumor cells were tested in singles, with candidate compounds at a concentration of 10 μM. Samples that showed at least 80% inhibition compared to cell and media and/or two standard deviations from the mean of the plate samples were advanced. In the first part of the second test (screen 2a), the compounds were re-tested, in duplicate, at 10 μM concentrations on patient tumors. Compounds that reconfirmed were then tested, in duplicate, at 10 μM concentration on patient normal cells. Samples that exhibited at least 80% inhibition on tumor cells and no more than 20% inhibition of normal cells were tested in the second part (screen 2b). At this level, the $IC_{50}$ of the remaining candidate compounds were assayed, in triplicate, on both patient tumor (screen 3a) and patient normal cells (screen 3b).

A summary of the results from this pilot screen is shown below:

| ANTI-TUMOR PILOT SCREEN RESULTS | | | |
| --- | --- | --- | --- |
| Tumor | Sarcoma | Lung | Colon |
| # compounds tested | 8,000 | 9,920 | 9,840 |
| Screen 1: # compounds with requisite result | 326 | 232 | 326 |
| Screen 2aT: # reconfirmed | 209 | 182 | 227 |
| Screen 2aN: # with requisite normal cell result | 40 | 30 | 34 |
| Screen 2b: # compounds with $IC_{50}$ no more than 500 nM | 6 | 8 | 6 |

To briefly summarize the results of the first phase of the screen, the "hit rate" in screen 1 ranged between 2.3% and 4.1%. Furthermore, throughout the run set, the coefficient of variation for the plate controls was approximately 10% (data not shown). The reconfirmation rate for the three tumors ranged between 64% and 78%. The percentage of active compounds that did not exhibit gross toxicity on normal cells was between 0.3% and 0.5% of the compounds tested in screen 1. Lastly, percentage of compounds that have $IC_{50}$ no more than 500 nM was approximately 0.08% of the compounds tested in screen 1.

Included in the pilot screen in a "blinded fashion" were 480 generic drugs including 13 anti-neoplastic compounds. None of the anti-neoplastic compounds passed the screen. Two compounds (cyclophospamide and methotrexate) would not have been anticipated to demonstrate in vitro activity. The remaining compounds either did not demonstrate at least 80% inhibition of tumor cells at 10 μM or showed greater than 20% inhibition of normal cells.

In an effort to discover additional compounds that are both potent and selective, upon completion of the first round of the screen, partial $IC_{50}$ were performed for both screens 2aT and 2aN. This allowed for the detection of compounds that may have failed the first round of testing because, the screen did not allow discovery of potent anti-tumor compounds that exhibited more than 20% inhibition of normal cells at 10 μm. Therefore, the 362 originally selected from screen 1 were tested in screen 2aT in duplicate at 1.0 μM, 100 nM, and 10 nM. Twenty compounds, five compounds, and four compounds, respectively, demonstrated at least 80% inhibition of tumor cells at these concentrations.

These 29 compounds were then tested in screen 2aN, in duplicate. Starting at 6.3 µM, five serial five-fold dilutions were tested. Based on these results, seven compounds were advanced to screen 2b where they were tested against tumor and normal cells, in triplicate, in eight half-log dilutions. A summary of the combined results for 13 of the compounds are shown in co-pending application Ser. No. 09/502,195. Three of the compounds identified in screen 2b are structural analogs of each other.

The three compounds that were structurally similar demonstrated anti-tumor activity and good potency. Upon testing a wider range of tumor types, the class of compound was demonstrated to be most active on sarcomas, ovarian carcinomas, and mesothelioma-type tumors. In comparison, the compounds were less active on colon and lung tumors, as well as melanomas and other tumors derived from stomach, kidney, and gall bladder (data not shown). Taken together, the data show that these compounds exhibit both anti-tumor activity and good potency.

Example 4

Identification of Additional Anti-tumor Compounds

The three compounds were subsequently identified as cardiac glycosides. (See co-pending application serial number to be assigned) We then tested digitoxin, another cardiac glycoside, to determine its anti-tumor efficacy.

Example 5

Phase II Evaluation of CP4071 in Previously Treated Advanced Sarcomas

A. Statement of Study Purpose: Rationale

1. To evaluate the efficacy, as measured by the response rate, of digitoxin given daily to patients with unresectable or metastatic sarcoma who have failed one or more prior treatment regimens.
2. To assess the clinical and laboratory toxicities of this dose/schedule of oral CP4071.
1. Background Soft tissue sarcomas represent 0.7% of all malignancies diagnosed in the United States, but the morbidity is great in that the peak incidence of these tumors is seen in children and young adults(1,2). A second peak occurs in late middle-age, resulting in significant morbidity in productive adults (2). Although the primary treatment of these tumors has improved, with limb-preserving surgery and radiation therapy resulting in improved functional ability, the treatment of metastatic disease is unsatisfactory and systemic chemotherapy as a post-surgical adjuvant is of unproven value(2). Only three agents—doxorubicin, ifosfamide and dacarbazine—are accepted as having useful activity in this group of diseases and combination chemotherapy regimens have not been demonstrated to result in a survival duration superior to that produced by therapy with single agents (2–6). Clearly, new agents with activity in soft tissue sarcomas need to be identified if therapy of these tumors is to improve.

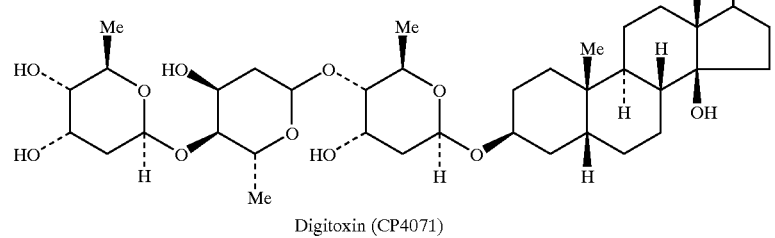

Digitoxin (CP4071)

Studies carried out on cells isolated from sarcoma patients demonstrated that the IC50 for digitoxin ranged from 13–48 nM, with a mean of 25 nM. Similar experiments with cells derived from ovarian tumor tissue demonstrated that the corresponding IC50 for digitoxin in these tumor samples ranged from 31–126 nM, with a mean of 47 nM. These data show that digitoxin can be used as an anti-neoplastic agent at relatively non-toxic concentrations.

Based on all of the above data, the present invention surprisingly provides needed methods and pharmaceutical compositions for treating mesotheliomas, sarcomas, carcinomas, stromal cell, and germ cell tumors.

Of the cardiac glycosides tested, digitoxin was determined to be the best drug for clinical trials in patients who have sarcomas. Digitoxin appeared more active in the assays then digoxin. Digitoxin and oubain were equally active but the oubain would need to be given by an intravenous infusion, as opposed to the convenience of orally available digitoxin.

1.1 Pharmacology

Digitoxin is extracted and crystallized from *Digitalis purpurea*. It has been used to treat cardiovascular disease for decades.

The activity of digitoxin on the myocardium is dose-related, and involves both a direct action on myocardium, the specialized conduction system and indirect actions on the cardiovascular system mediated by the autonomic nervous system. These indirect actions involve a vagomimetic action (depression of atrioventricular node and a baroreceptor sensitization) that results in increased carotid sinus nerve activity and enhanced sympathetic withdrawal for any given increment in mean arterial pressure.

Digitalis has a direct inotropic effect on the myocardium At higher doses digitalis increases sympathetic outflow from the CNS to both cardiac and peripheral sympathetic nerves. The result may be increased atrial or ventricular rates, possibly an important factor in digitalis cardiac toxicity.

The cellular basis for the inotropic effects of the digitalis glycosides appears to be inhibition of sodium and potassium ATPase in the sarcolemma, which alters excitation-contraction coupling. By inhibiting sodium and potassium-ATPase the digitalis glycosides make more calcium available to activate the contractile proteins, actin and myosin.

The mechanism of the antitumor activity of cardiac glycosides is not known.

1.2 Pharmacokinetics

Digitoxin is greater than 90% absorbed following oral administration. When taken with food, absorption is slowed but complete, except when taken with meals high in bran fiber.

Cardiac glycosides are widely distributed in tissues. High concentrations are found in the myocardium, skeletal muscle, liver, brain and kidneys.

Fifty-80% of administered digitoxin is degraded by the liver to inactive metabolites that are excreted by the kidneys. About 8% is converted to digoxin.

Digitoxin has a serum half life of 7–9 days. As a result, clinical effects do not fully develop until steady state levels (approximately 5 half lives) are achieved, and 3–5 weeks are needed for complete dissipation of digitoxin effects following discontinuation. Digitoxin is greater than 95% bound to plasma proteins. The bound drug is in equilibrium with the unbound fraction. At equilibrium, the concentrations in cardiac tissue are 15 to 30 times those in the plasma; the concentration in skeletal muscle is about half that in the heart. Digitoxin is not effectively removed by peritoneal or hemodialysis, probably due to its high degree of plasma protein binding.

2. Study Rationale

Both in vitro and epidemiological data suggest that the cardiac glycosides have antitumor activity. Since the risks of digitoxin administration are well known in humans, it is appropriate to determine if doses routinely used to treat patients with cardiac disorders are sufficient to achieve an antitumor effect in patients with various sarcomas.

3. Study Drug 3.1 CP4071 (digitoxin) is a single cardiac glycoside extracted from the leaves of *Digitalis purpurea*. Digitoxin is: card-20 (22)-enolide,3-[(O-2,6-dideoxy-β-D-ribo-hexopyranosy-(1–4)-2,6-dideoxy-β-D- ribo-hexopyranosy)oxy]-14 hydroxy, (3β,5β). Digitalis has been used to treat cardiovascular disease for many decades.

3.2 Source of Drug: Digitoxin (Medisca). Will be provided by the pharmacist as a liquid. It is formulated to contain 0.05 mg digitoxin/ml, 20% ethanol (USP), 10% propylene glycol, 200 mg aspartame and créme de mint qs ad 8 oz water. The digitoxin will be provided in capped syringes each containing a single premeasured dose of drug which can be either taken directly or first diluted in a small amount of liquid.

3.3 Drug Dosage: Eligible patients initially will be slowly digitalized, with 4 ml (0.2 mg) digitoxin twice daily for 4 days, followed by a maintenance dosage of 1 ml (0.05) to 6 ml (0.3 mg). The initial maintenance dose will be 0.15mg daily. If after six weeks at 3 ml (0.15 mg) daily there is no evidence of digitalis toxicity (ECG, digitoxin blood level, GI or visual symptoms, the maintenance dose may be increased to 4 ml (0.2 mg) daily. If after six weeks at 4 ml (0.2 mg) daily there is no evidence of digitalis toxicity (ECG, digitoxin blood level, GI or visual symptoms), the maintenance dose may be increased to 5 ml (0.25 mg) daily. All patients must start at the 3 ml (0.15 mg) digitoxin dose and may be escalated to the 5 ml (0.25 mg) dose if tolerated in the above schedule. If a patient experiences a Grade 3 or Grade 4 arrythmia, the digitoxin dose will be withheld. Once resolved, the patient may be restarted at the next lower non cardiotoxic dose.

3.5 Precautions 3.5.1.Electrolyte imbalance:

Potassium—Hypokalemia sensitizes the myocardium to digitalis. Toxicity may develop even with serum glycoside levels in the "normal" range. Therefore, it is important to maintain normal serum potassium levels. Potassium wastage may results from diuretic or corticosteroid therapy, hemodialysis or from suction of gastrointestinal secretions. It may also accompany malnutrition, diarrhea, prolonged vomiting, old age or long-standing congestive heart failure. Infusion of carbohydrate solution may lower serum potassium by causing an intracellular shift of potassium. In general avoid rapid shifts in serum potassium or other electrolytes.

Calcium—Hypercalcemia from any cause predisposes the patient to digitalis toxicity. The effect of cardiac glycosides on the myocardium are reduced by hypocalcemia.

Magnesium—Hypomagnesemia may predispose to digitalis toxicity. If low magnesium levels are detected, magnesium levels will be restored with oral or intravenuous supplementation as required.

3.5.2. Cardiac Problems

Patients with incomplete AV block, especially subject to Stokes-Adams syndrome may develop advanced or complete heart block. Patients with acute myocardial infarction, severe pulmonary disease, severe carditis (e.g. carditis associated with rheumatic fever or viral myocarditis) or advanced heart failure may be more sensitive to digitalis and prone to rhythm disturbances.

Drug Interactions

A variety of drugs may affect the serum concentration of cardiac glycosides via various mechanisms (eg, altered GI flora, decreased clearance.) possibly increasing its therapeutic or toxic effects.

Beta blockers: These drugs may inhibit AV nodal conduction and can result in complete heart block.

Nondepolarizing muscle relaxants and succinylcholine: When administered with digitalis glycosides, cardiac arryhthmias may be increased.

Potassium-sparing diuretics: Spironolactone may increase or decrease toxic effects of digitalis glycosides. Changes cannot be predicted and patients should be carefully monitored. Amiloride may decrease inotropic effects of digoxin; triamterene may increase its pharmacological effects.

Sympathomimetics: Concomitant use with digitoxin can increase the risk of cardiac arrhythmias because both enhance ectopic pacemaker activity.

Thiazide and loop diuretics and amphotheracin B increase potassium loss, possibly resulting in hypokalemia and will be used with caution in patients receiving CP4071.

Thyroid hormones: Thyroid hormones may decrease the therapeutic effectiveness of cardiac glycosides, and thioarnines may increase their therapeutic and toxic effects.

3.5.3 Contraindications

A previous toxic response to digitalis preparations, ventricular fibrillation, ventricular tachycardia, beriberi heart disease, allergy to digitalis, although rare may occur and some cases of hypersensitive carotid sinus syndrome.

Pregnancy: Category C. Digitoxin rapidly crosses to the fetus in a concentration 50–83% of maternal serum. Effects on reproductive capacity and fetal harm are unknown.

3.5.4 Laboratory Tests Determinations of heart rate, electrolytes (especially magnesium, potassium and calcium) and ECG will be determined (cf Table I) and whenever required in evaluating the patient's condition.

Serum digitoxin levels: —Serum digitoxin levels will be determined (cf Study Calendar) at two week intervals or if there is a suggestion of digitalis toxicity. Samples should be obtained (trough levels) just before the daily dose. The therapeutic concentration is 10–35 ng/mL (13–46 nM). However, the steady-state serum concentration should only be interpreted in relation to the overall clinical evaluation of the patient. An isolated serum concentration value alone will not be used as a basis for increasing or decreasing the digitoxin dose.

B. Description of Study Design and Statistical Analysis

4. Methods for Selecting Subjects:
4.1 All patients must have a pathologically verified diagnosis of soft tissue sarcoma with histologic, cytologic or clinical evidence of metastatic or locally advanced disease (Stage IV or recurrent). Patients with, Kaposi's sarcomas, sarcomas of bone or mesotheliomas are not eligible. Please see Staging Criteria, below.
4.2 Patients must have received no more than three prior chemotherapy regimens for advanced, recurrent or metastatic disease. Prior biologic response modifier treatment will be allowed.
4.3 Patients must have unidimensionally measurable lesions by x-ray, scans (CT or MRI) or physical examination documented within 28 days prior to registration. Patients with CNS metastases are not eligible.
4.4 Prior radiation therapy will be allowed. At least 3 weeks must have elapsed since the administration of the last fraction of radiation therapy and patients must have recovered from all associated toxicities. The measurable disease site should be outside of previously irradiated fields.
4.5 Patients must have a Southwest Oncology Group Performance Status of 0–2.
4.6 Patients must have either serum creatinine less than 1.5 times the institutional upper limit of normal, and serum calcium less than the institutional upper limit of normal, and serum potassium within normal limits, obtained within 14 days prior to registration.
4.7 Patients with heart disease already on a cardiac glycoside are not eligible.
4.8 Patients must have adequate hepatic function as defined by a serum bilirubin, up to 2.5× the institutional upper limit of normal (ULN).
4.9 Patients may have received prior surgery. At least 4 weeks must have elapsed and patients must have recovered from all side-effects associated with surgery.
4.10 Pregnant or nursing women may not participate. Women/men of reproductive potential may not participate unless they have agreed to use an effective contraceptive method.
4.11 Patients may not receive concurrent radiation therapy, hormonal therapy for malignancy or other chemotherapy while on this protocol.
4.12 Patients must be physically, mentally and emotionally able to give informed consent.
4.13 No other prior malignancy is allowed except for the following: adequately treated basal cell or squamous cell skin cancer, in situ cervical cancer, adequately treated Stage I or II cancer from which the patient is currently in complete remission, or any other cancer from which the patient has been disease-free for 5 years.
4.14 If day 14 or 28 falls on a weekend or holiday, the limit may be extended to the next working day. In calculating days of tests and measurements, the day a test or measurement Is done is considered to be Day 0. Therefore, if a test is done on a Monday, the Monday two weeks later would be considered Day 1.
4.17 Patients must be informed of the investigational nature of this study and must sign and give written informed consent in accordance with institutional and federal guidelines.

5. Statistical Considerations
5.1. This is a pilot Phase II, non-randomized, single-armed study. The expected accrual rate is 5–6 patients per month. The duration of the study is anticipated to be 12 months; the duration of each subject's participation is likely to be twelve to eighteen months (the approximate duration of time to failure in sarcoma patients responding to agents known to be effective). Tumor measurements will be repeated on each patient at three to six week intervals.
5.2 . A response probability of 20% would be of interest, while further testing would not be pursued if the response probability is 5% or lower. Initially, 14 patients will be entered. If at least one response is observed, an additional 11 patients will be entered. 5 or more responses out of 25 will be considered as evidence warranting further study of this regimen provided other factors, such as toxicity and survival also appear favorable. This design has a significance level (probability of falsely declaring an agent with a 5% response probability to warrant further study) of 5%, and a power (probability of correctly declaring an agent with a 20% response probability to warrant further study) of 94%.

| True Response Probability | 5% | 10% | 15% | 20% |
|---|---|---|---|---|
| Probability of stopping early | 36% | 12% | 4% | 1% |
| Probability of declaring agent warrants further study | 5% | 37% | 73% | 92% |

5.3. 25 patients are insufficient to estimate the probability of a particular toxicity to within ±0.16 (40 patients would be required for this). However, any toxicity occurring with at least 10% probability is likely to be seen at least once (87% chance).

6.0 Description of Study Procedures:
6.1 Pretreatment requirements are to be completed as listed on the Study Calendar, Section 9.0.
6.2 A baseline CT or MRI scans deemed relevant to tumor evaluation will be obtained, and repeated at 6 week intervals during treatment.
6.3 Drug Administration: All patients will initially receive the same treatment. Digitoxin solution, 0.2 mg will be administered orally twice a day for 4 days. On day 5 a daily maintenance dose of 0.15 mg will be started. If at six weeks there is no evidence of digitalis toxicity, the maintenance dose may be increased to 0.20 mg daily. If after a further six weeks there is no evidence of digitalis toxicity, the maintenance dose may be increased to 0.25 mg daily.
6.4 Serum digitoxin levels will be obtained just before daily dose every six weeks or whenever there is any suggestion of digitalis toxicity.

6.5 Responding or stable disease patients will continue on study until tumor progression.

6.6 Criteria For Removal From Protocol Treatment.
  a. Progression of disease (as defined in Section 10.1d.5).
  b. Delay of treatment greater than 2 weeks.
  c. Unacceptable toxicity requiring discontinuation of chemotherapy (ECG evidence of digitalis toxicity) (see Section 8.0).

6.7 The patient may withdraw from the study at any time for any reason. All reasons for discontinuation of treatment must be documented in the Flow Sheets.

6.8 All patients will be followed until death.

6.9 Supportive Therapy, toxicities to be monitored, and dosage modifications:

It is important that the patient ingest an adequate amount of potassium daily. Foods high in potassium, such a bananas, may be an adequate source.

Other Concomitant Medication: No other concomitant medications should be given except analgesics, chronic treatments for concomitant medical conditions, or agents required for life-threatening medical problems. All medications prescribed should be checked for drug interactions.

Patient Information

Avoid over the counter antacids, cough, cold, allergy and diet drugs unless approved by the investigator(s). Notify physician if loss of appetite, lower stomach pain, nausea, vomiting, diarrhea, unusual tiredness or weakness, drowsiness, headache, blurred or yellow vision, skin rash or hives or mental depression occurs.

7.0 Dose Adjustments: guidelines which follow outline dose adjustments for several of these toxic effects.

IF A PATIENT EXPERIENCES SEVERAL TOXICITIES AND THERE ARE CONFLICTING RECOMMENDATIONS, PLEASE FOLLOW THE MOST CONSERVATIVE DOSE ADJUSTMENT RECOMMENDED.

DOSES WHICH HAVE BEEN REDUCED FOR TOXICITY SHOULD NOT BE RE-ESCALATED BACK TO STARTING LEVEL.

7.1 Gastrointestinal: Most common early symptoms are anorexia, nausea, vomiting and diarrhea. Abdominal discomfort or pain often accompanies GI symptoms. Digitalis toxicity very rarely may cause hemorrhagic necrosis of the intestines.

7.2 CNS: Headaches, weakness, apathy, drowsiness, visual disturbances (blurred, yellow vision, halo effect), confusion, restlessness, disorientation, seizures, EEG abnormalities, delirium, hallucinations, neuralgia, psychosis.

7.3 Cardiac disturbances: Ventricular tachycardia may result from digitalis toxicity. Unifocal or multiform premature ventricular contractions, especially in begeminal or trigeminal patterns, are the most common toxic arrhythmias. Paroxysmal dysrythmias, nodal rhythms, AV dissociation, accelerated junctional (nodal) rhythm and paroxysmal atrial tachycardia with block are also common. Excessive slowing of the pulse is a clinical sign of overdose. AV block of increasing degree may proceed to complete heart block. Atrial fibrillation can occur following large doses of digitalis. Ventricular fibrillation is the most common cause of death from digitalis poisoning. The ECG is essential in determining the presence and nature of these cardiac disturbances.

7.4 Hypokalemia: Administer potassium chloride intravneouslty or in divided oral doses.

7.5 Digitoxin will be held if there is evidence of cardiac toxicity. . The decision to reduce the dose or discontinue therapy with digitoxin will be made in conjunction with a cardiac consultant.

7.6 Unexpected or fatal toxicities (including suspected reactions) must be reported to the Operations Office, to the Study Coordinator, and to the IRB.

8.0 Criteris for Evaluation and Endpoint Definitions

Definitions:
  a. Measurable Disease: Unidimensionally measurable lesions with clearly defined margins by: 1) medical photograph (skin or oral lesion), or plain x-ray with at least one diameter 0.5 cm or greater (bone lesions are not included) or, 2) CT, MRI or other imaging scan with at least two diameters greater than the distance between cuts of the imaging study, or 3) palpation with 2 diameters 2 cm or greater, although only one diameter selected initially need be measured.
  b. Evaluable Disease: Masses with margins not clearly defined, lesions with both diameters less than 0.5 cm, lesions on scan with either diameter smaller than the distance between cuts, palpable lesions with either diameter less than 2 cm, bone disease.
  c. Non-Evaluable Disease: Pleural effusions, ascites, disease documented by indirect evidence only (e.g., by lab values).
  d. Objective Status, To Be Recorded at Each Evaluation: If an organ has too many measurable lesions to measure at each evaluation, choose three to be followed before the patient is entered on study. The remaining measurable lesions in that organ will be considered evaluable for the purpose of objective status determination. Unless progression is observed, objective status can only be determined when ALL measurable and evaluable sites and lesions are assessed.

8.1 Complete Response (CR): Complete disappearance of all measurable and evaluable disease. No new lesions. No disease related symptoms. No evidence of non-evaluable disease, including normalization of markers and other abnormal lab values. All measurable, evaluable and non-evaluable lesions and sites must be assessed using the same techniques as baseline. Refers to clinical CR—when restaging surgery is required, a separate pathologic response variable is incorporated in the response data.

8.2 Partial Response (PR): Applies only to patients with at least one measurable lesion: Greater than or equal to 50% decrease under baseline in the sum of products of perpendicular diameters of all measurable lesions. No progression of evaluable disease. No new lesions. All measurable and evaluable lesions and sites must be assessed using the same techniques as baseline.

8.3 Partial Response, Non-Measurable (PRNM): Not applicable.

8.4. Stable/No Response: Does not qualify for CR, PR, or progression. All measurable and evaluable sites must be assessed using the same techniques as baseline.

8.5. Progression: 50% increase or an increase of 10 cm2 (whichever is smaller) in the sum of products of all measurable lesions over smallest sum observed (over baseline if no decrease) using the same techniques as baseline, OR clear worsening of any evaluable disease, OR reappearance of any lesion which had disappeared, OR appearance of any new lesion/site, OR failure to return for evaluation due to death or deteriorating condition (unless clearly unrelated to this cancer). For "scan only" bone disease, increased uptake does not constitute clear worsening. Worsening of existing non-evaluable disease does not constitute progression.

8.6 Exceptions: (1) In cases for which initial tumor flare reaction is possible (hypercalcemia, increased bone pain, erythema of skin lesions), either symptoms must persist beyond four weeks or there must be additional evidence of progression. (2) Lesions which appear to increase in size due to presence of necrotic tissue will not be considered to have progressed.

8.7. Unknown: Progression has not been documented and one or more measurable or evaluable sites have not been assessed.

8.8 Notes:

a. Non-evaluable disease does not affect objective status except in determination of CR (must be absent—a patient who otherwise has a CR, but who has non-evaluable disease present or not assessed, will be classified as having a PR), and in determination of progression (if NEW sites of non-evaluable disease develop). Patients with only non-evaluable disease cannot be assessed for response.

b. For evaluable disease other than types specified in Section 10.1d.3, the only objective statuses which apply are CR, stable/no response, progression and unknown.

c. Objective statuses must stay the same or improve over time until progression (unknown excepted).

d. PR and PRNM cannot apply to the same patient.

e. Best Response: This will be calculated from the sequence of objective statuses.

For patients with all disease sites assessed every three to six weeks, two objective status determinations of CR before progression are required for a best response of CR. Two determinations of PR or better before progression, but not qualifying for a CR, are required for a best response of PR. Two determinations of stable/no response or better before progression, but not qualifying as CR, PR or PRNM, are required for a best response of stable/no response; if the first objective status is unknown, only one such determination is required. Patients with an objective status of progression on or before the second evaluation (second AFTER the pre-study evaluation) will have a best response of increasing disease. Best response is unknown if the patient does not qualify for a best response of increasing disease and if all objective status determinations after the first determination and before progression are unknown.

For patients with disease scheduled to be assessed only at greater than six week intervals, only one assessment of stable/no response or better before progression, but not qualifying for a CR, PR or PRNM is required for a best response of stable/no response. For CR, PR or PRNM response must be confirmed; a second assessment should be scheduled for four weeks after the first documentation of response. Patients with objective status of progression at the first evaluation will have a best response of increasing disease. Best response is unknown if the patient does not qualify for best response of increasing disease and all objective status determinations before progression are unknown.

f. Performance Status: Patients will be graded according to the current Southwest Oncology Group grading scale:

Grade Scale

0 Fully active; able to carry on all predisease activities without restriction.

1 Restricted in physically strenuous activity but ambulatory and able to carry out work of a light or sedentary nature, e.g., light housework, office work.

2 Ambulatory and capable of all self-care but unable to carry out any work activities. Up and about more than 50% of waking hours.

3 Capable of only limited self-care; confined to bed or chair more than 50% of waking hours.

4 Completely disabled. Cannot carry on any self-care. Totally confined to bed or chair.

5 Dead g. Time to Treatment Failure: From date of registration to date of first observation of progressive disease (as defined in 10.1d.5), death due to any cause, or early discontinuation of treatment.

h. Time to Death: From date of registration to date of death due to any cause.

9.0 Bibliography for Example 5

1. Boring C C, Squires T S, Tong T. Cancer statistics C A 41:19–39, 1991.
2. Yan J C, Glatstein E, Rosenberg S A, Antman D H. Sarcomas of soft tissues, in: Cancer: Principles & Practice of Oncoiogy, Fourth Edition. DeVita V T, Jr.$_1$ Heilman S, Rosenberg S A (eds). J B Lippincott, Philadelphia, 1436–1488, 1993.
3. Borden E C Arnato D A, Rosenbaum C, Enterline H T, Shiraki M J, Creech R H, Lerner H-I, Carbone P P. Randomized comparison of three Adriamycin regimens for metastatic soft tissue sarcomas. J Clin Onc 5:840–50, 1987.
4. Omura G A, Major F J, Blessing J A, Sedlacek T V, Thigpen J T, Creasman W T, Zaino R J. A randomized study of Adriamycin with and without dimethytriazenoe-imidazole carboxamide in advanced uterine sarcoma. Cancer 52:62–632, 1983.
5. Edmonson J H, Ryan L M, Blum R H, Brooks J S J, Shiraki M, Frytak S, Parkinson D R. Randomized comparison of doxorubicin alone versus ifosfamide plus doxorubicin or mitomycin, doxorubicin and cisplatin against advanced soft tissue sarcomas. J Clin Onc 11:1269–1275, 1993.
6. Antman K, Crowley J, Balcerzak S P, et al. An intergroup Phase Ill randomized study of doxorubicin and dacarbazine with or without ifosfamide and mesna in advanced soft tissue and bone sarcomas. J Clin Onc 11:127–1285, 1993.
7. Repke K R H, Schon R, Megges R et al. Potential suitability of $Na^+/K^+$-transporting ATPase in pre-screens for anti-cancer agents. Anti-Cancer Drugs Design 10:177–187, 1995.
8. Gheorghiade M, Pitt B. Digitalis Investigation Group (DIG) trial: A stimulus for further research. Am Heart J 134:3–12, 1997.
9. Garg R, Gorlin R, Smith T et al. The effect of digoxin on mortality and morbidity inpatients with heart failure. N Engl J Med 336:525–533, 1997.
8. Hyun J-W, Shin J-E, Lim K-H et al. Evomonoside: The cytotoxic cardiac glycoside from Lepidium apetalum. Planta Med 61:294–295, 1995.
9. Inada A, Nakanishi T, Konoshima T, et al. Anti-tumor promoting activities of natural products. II. Inhibitory effects of digitoxin on two-stage carcinogenesis of mouse skin tumors and mouse pulnonary tumors. Biol. Pharm. Bull 16:930–931, 1993.
10. Stenkvist B, Bengtsson E, Eriksson O et al. Cardiac glycosides and breast cancer. Lancet Mar 10; 1(8115):563, 1979.
11. Stenkvist B, Bengtsson E, Eklund G et al. Evidence of a modifying influence of heart glucosides on the development of breast cancer. Analytical and Quantitative Cytology 2:49–54, 1980.
12. Stenkvist B, Bengtsson E, Dahlqvist B et al. Cardiac glycosides and breast cancer, revisited. N Engl J Med 306:484.
13. Goldin A G, Safa A R. Digitalis and Cancer. Lancet May 19;1 (8386):1134, 1984.

14. Friedman G D. Digitalis and Breast Cancer. Lancet Oct 13;2 (8407):875, 1984.
17. Stenkvist B. Is digitalis a therapy for breast carcinoma: Oncol Rep 6:493–496, 1999.

Example 6

A Phase II Trail of CP 4071 in Patients with Recurrent Epithelial Mullerian Adenocarcinoma I. Objectives
A. To determine response rate and toxicity of CP4071 in patients with recurrent epithelial mullerian cancer.
B. To assess the clinical and laboratory toxicities of this dose/schedule of CP4071.

II. Background and Rationale

In 1999, it is estimated that there will be 25,200 cases of ovarian cancer diagnosed in the United States (1). The majority of these patients present with advanced stage epithelial neoplasms where the management includes aggressive cytoreductive surgery and cytotoxic chemotherapy. Despite innovative surgical strategies and multi-agent chemotherapy, patients will experience recurrence of the ovarian cancer.

Previous studies by the Gynecologic Oncology Group established the superiority of cisplatin and paclitaxel over cisplatin and cyclophosphamide for the initial treatment of advanced stage epithelial ovarian cancer (2). Subsequent investigators demonstrated that carboplatin/paclitaxel is equivalent to cisplatin/paclitaxel when treating these patients (3). Despite prolongation of median progression free and overall survival, many of these patients will experience recurrent disease. Though many therapeutic options are available for recurrent disease, there is no consensus as to the optimal regimen. One must consider efficacy, toxicity, route of administration and cost when deciding how to treat each individual patient. There definitely is a need for more effective and less toxic treatment for patients with recurrent ovarian carcinoma.

Study Rationale

Both in vitro and epidemiological data suggest that the cardiac glycosides have antitumor activity. Since the benefits and safety of digitoxin administration are well known in humans, it is appropriate to determine if doses routinely used to treat patients with cardiac disorders are sufficient to achieve an antitumor effect in patients with recurrent mullerian epithelial adenocarcinoma.

III. Experimental Plan
  A. Study Design
    1. Phase II
    2. Digitoxin
    3. Non-randomized
    4. Multicenter
    5. No stratification
    6. Endpoints:
      a) Maximum tolerated dose
      b) Efficacy
      c) Toxicity
  Number of patients: 40
  Estimated study duration: 12 months IV. Patient Eligibility and Enrollment
  A. Inclusion Criteria.
    1. Patients must have been previously treated at least once with a platinum analogue and paclitaxel prior to entry.
    2. Patients with a histologic diagnosis of recurrent ovarian, tubal, or peritoneal cancer or a CA125>100 in patients who have a history of ovarian, tubal or peritoneal cancer.
    3. Patients must have received no more than three prior chemotherapy regimens for advanced, recurrent or metastatic disease. Prior biologic response modifier treatment will be allowed.
    4. Patients must have bidimensionally measurable lesions by x-ray, scans (CT or MRI), physical examination documented within 28 days prior to registration. Patients with CNS metastases are not eligible. Alternatively, patients with serum CA125 levels over 100 with no measurable disease may be enrolled in this study.
    5. Prior radiation therapy will be allowed. At least 3 weeks must have elapsed since the administration of the last fraction of radiation therapy and patients must have recovered from all associated toxicities. The measurable disease site should be outside of previously irradiated fields.
    6. Adequate bone marrow, renal and hepatic function as defined by WBC greater than 3,000 cells/cu.ml., platelets greater than or equal to 100,000/cu.ml., creatinine less than 1.5 mg/dl, total bilirubin less than or equal to 2 mg/dl, AST/ALT/alkaline phosphatase level <two times the upper limit of normal in the absence of liver metastasis or <five times the upper limit of normal if liver metastasis was present.
    7. Gynecologic Oncology Group (GOG) performance status less than or equal to 2 (see Appendix I).
    8. Patients who have signed an approved informed consent.
  B. Exclusion Criteria
    1. Patients with epithelial ovarian cancer of low malignancy potential.
    2. Patients with septicemia, severe infection, or acute hepatitis.
    3. Patients with severe gastrointestinal bleeding.
    4. Patients with a past or concomitant malignancy other than skin (excluding melanoma).
    5. Patients with heart disease already on a cardiac glycoside are not eligible.
    6. Patients with known cardiac disease, not already on a cardiac glycoside, may be enrolled unless they have idiopathic hypertrophic stenosis.
    7. Patients with hypokalemia are not eligible until serum potassium level is within the normal range.
    8. Pregnant or nursing women may not participate. Women of reproductive potential may not participate unless they have agreed to a pregnancy test and to use an effective contraceptive method.

Following determination of eligibility and acquisition of signed informed consent, patients are deemed eligible for protocol entry.

Patients will be followed by their gynecologic oncologist to assess efficacy of the medication with regards to their ovarian cancer. Cardiologists will follow the patients digitoxin levels, ECG's, and assess patients for evidence of digitoxin toxicity.

V. Criteria for Evaluation and Endpoint Definitions
  A. Definitions.
    1. Measurable Disease: Bidimensionally measurable lesions with clearly defined margins by 1) medical photograph (skin or oral lesion) or plain x-ray with at least one diameter 0.5 cm or greater (bone lesions are not included), or 2) CT, MRI or other imaging scan with both diameters greater than the distance between cuts of the imaging study, 3) palpation with both diameters 2 cm or greater, or 4) CA 125 greater than 100.
2. Evaluable Disease: Unidimensionally measurable lesions, masses with margins not clearly defined, lesions with both diameters less than 0.5 cm, lesions on scan with either diameter smaller than the distance between cuts, palpable lesions with either diameter less than 2 cm, bone disease.
3. Non-Evaluable Disease: Pleural effusions, ascites.
4. Complete Response (CR): A clinical complete response requires the complete disappearance of all known measurable and evaluable disease determined by two measurements not less than four weeks apart. A serologic complete response will be defined by the decline of the previously elevated CA 125 declined to within normal limits on two successive measurements three weeks apart. Refers to clinical CR—when restaging surgery is required, a separate pathologic response variable is incorporated in the response data.
5. Partial Response: A clinical partial response will be defined by greater than 50% decrease in the sum of the products of the greatest length and perpendicular width of all measurable lesions for at least four weeks, with no simultaneous increase in evaluable disease during this period. A serologic partial response will be defined by a 50% decrease in the previously elevated CA 125 which is confirmed on repeat analysis 3 weeks later. All measurable and evaluable lesions and sites must be assessed using the same techniques as baseline.
6. Stable Disease: State of response that is less than partial response or progression and lasts for at least eight weeks with no clinical evidence of progression.
7. Progression: 50% increase or an increase of 10 $cm^2$ (whichever is smaller) in the sum of products of all measurable lesions over smallest sum observed (over baseline if no decrease) using the same techniques as baseline, OR clear worsening of any evaluable disease, OR reappearance of any lesion which had disappeared, OR appearance of any new lesion/site, OR failure to return for evaluation due to death or deteriorating condition (unless clearly unrelated to this cancer) OR doubling of CA 125 which is confirmed on repeat analysis three weeks later. For "scan only" bone disease, increased uptake does not constitute clear worsening. Worsening of existing non-evaluable disease does not constitute progression.
8. Unknown: Progression has not been documented and one or more measurable or evaluable sites have not been assessed.

Exceptions:

(1) In cases for which initial tumor flare reaction is possible (hypercalcemia, increased bone pain, erythema of skin lesions), either symptoms must persist beyond four weeks or there must be additional evidence of progression.
(2) Lesions which appear to increase in size due to presence of necrotic tissue will not be considered to have progressed.

Notes:

a. Objective Status, To Be Recorded at Each Evaluation: If an organ has too many measurable lesions to measure at each evaluation, choose three to be followed before the patient is entered on study. The remaining measurable lesions in that organ will be considered evaluable for the purpose of objective status determination. Unless progression is observed, objective status can only be determined when ALL measurable and evaluable sites and lesions are assessed.

b. Non-evaluable disease does not affect objective status except in determination of CR (must be absent—a patient who otherwise has a CR, but who has non-evaluable disease present or not assessed, will be classified as having a PR), and in determination of progression (if NEW sites of non-evaluable disease develop). Patients with only non-evaluable disease cannot be assessed for response.

c. For evaluable disease other than types specified in Section V.A., the only objective statuses which apply are CR, stable/no response, progression and unknown.

d. Objective statuses must stay the same or improve over time until progression (unknown excepted).

e. PR and PRNM cannot apply to the same patient.

f. Best Response: This will be calculated from the sequence of objective statuses.

For patients with all disease sites assessed every three to six weeks, two objective status determinations of CR before progression are required for a best response of CR. Two determinations of PR or better before progression, but not qualifying for a CR, are required for a best response of PR. Two determinations of stable/no response or better before progression, but not qualifying as CR, PR or PRNM, are required for a best response of stable/no response; if the first objective status is unknown, only one such determination is required. Patients with an objective status of progression on or before the second evaluation (second AFTER the pre-study evaluation) will have a best response of increasing disease. Best response is unknown if the patient does not qualify for a best response of increasing disease and if all objective status determinations after the first determination and before progression are unknown.

For patients with disease scheduled to be assessed only at greater than six week intervals, only one assessment of stable/no response or better before progression, but not qualiing for a CR, PR or PRNM is required for a best response of stable/no response. For CR, PR or PRNM response must be confirmed; a second assessment should be scheduled for four weeks after the first documentation of response. Patients with objective status of progression at the first evaluation will have a best response of increasing disease. Best response is unknown if the patient does not qualify for best response of increasing disease and all objective status determinations before progression are unknown.

g. Time to Treatment Failure: From date of registration to date of first observation of progressive disease (as defined in 10.1d.5), death due to any cause, or early discontinuation of treatment.

VI. STUDY DRUG

See Example 5.

A. Pharmacokinetics: See Example 5
B. Toxicity: See Example 5
C. Precautions
1 Electrolyte imbalance:
   a) Potassium—See Example 5. Potassium chloride in divided oral doses of 3–6 gm (40–80 mEq) daily may be given if renal function is adequate. Do not use potassium when severe or complete heart block is due to digitalis.
   b) Calcium—See Example 5.
   c) Magnesium—Hypomagnesemia may predispose to digitalis toxicity. If low magnesium levels are detected, institute replacement therapy.
D. Laboratory Tests:
1. Periodic determinations of heart rate, electrolytes (especially potassium and calcium) and ECG will be determined (Table 1) and whenever required in evaluating the patient's condition.
2. Serum digitoxin levels:—Serum digitoxin levels will be determined. Samples should be obtained (trough levels) just before the daily dose. The therapeutic concentration is 10–35 ng/mL (13–46 nM). However, the steady-state serum concentration should only be interpreted in the overall clinical evaluation of the patient. Do not use an isolated serum concentration value alone as a basis for increasing or decreasing the digitoxin dose.
E. Drug Interactions: See Example 5
F. Contraindications: See Example 5
1. A previous toxic response to digitalis preparations, ventricular fibrillation, pregnancy, ventricular tachycardia, beriberi heart disease, allergy to digitalis, although rare may occur and some cases of hypersensitive carotid sinus syndrome.
2. Pregnancy: See Example 5.
3. Concomitant medications: See Example 5.

VII. Study Procedures
A. If anytime during study a tissue sample is obtained, a portion will be stored frozen at −70° C. for possible determination of tissue digitoxin levels and an additional portion stored at 4° C. for chemosensitivity testing.
B. The patient may withdraw from the study at any time for any reason.
C. All reasons for discontinuation of treatment must be documented in the Flow Sheets.
D. The development of any evidence of cardiac toxicity will result in a discontinuation of digitoxin. The decision to reduce the dose or discontinue therapy with digitoxin will be made in conjunction with a cardiac consultant if necessary.
E. Serum digitoxin levels will be obtained just before the daily dose every four weeks or whenever any suggestion of digitalis toxicity.
F. Other Concomitant Medication: No other concomitant medications should be given except analgesics, chronic treatments for concomitant medical conditions, or agents required for life-threatening medical problems. Before prescribing any concomitant medication, review VI.F. (Drug Interactions).

VIII. Study Design and Statistical Analysis
A. If day 14 or 28 falls on a weekend or holiday, the limit may be extended to the next working day and is considered to be Day 0. Therefore, if a test is done on a Monday, the Monday two weeks later would be considered Day 14.
B. Patients must be informed of the investigational nature of this study and must sign and give written informed consent in accordance with institutional and federal guidelines.

IX. Dosage Determination
A. Eligible patients initially will be slowly digitalized, with 4 ml (0.2 mg) digitoxin twice daily for 4 days, followed by a maintenance dosage of 1 ml (0.05) to 6 ml (0.3 mg). The initial maintenance dose will be 0.15 mg daily. If after four weeks at 3 ml (0.15 mg) daily there is no evidence of digitalis toxicity (ECG, digitoxin blood level, GI or visual symptoms, the maintenance dose may be increased to 4 ml (0.2 mg) daily. If after four weeks at 4 ml (0.2 mg) daily there is no evidence of digitalis toxicity (ECG, digitoxin blood level, GI or visual symptoms), the maintenance dose may be increased to 5 ml (0.25 mg) daily. All patients must start at the 3 ml (0.15 mg) digitoxin dose and may be escalated to the 5 ml (0.25 mg) dose if tolerated in the above schedule.
B. If a patient experiences a Grade 3 or Grade 4 arrhythmia, the digitoxin dose will be withheld. Once resolved, the patient may be restarted at the next lower non cardiotoxic dose.

X. Efficacy Determination
A. Response Rate: That proportion of patients who responded to treatment with complete response or partial response.
B. Response Duration: The time from the initial documented response to the first sign of disease progression.
C. Time to Progression: The time from initial administration of study medication to documented disease progression.
D. Time to Response: The time from the first infusion of study medication to the time of initial documented response.
E. Survival: The time from the first dose of study medication until death due to any cause.

XI. Laboratory Studies
A. Pretreatment laboratory studies included a complete blood count, electrolytes, BUN, creatinine, glucose, total protein, albumin, calcium, phosphate, uric acid, alkaline phosphatase, total and direct bilirubin, ALT, AST and amylase.

XII. Adverse Events
A. Definitions:
1. Serious adverse event: any experience that is fatal or life-threatening, requires or extends inpatient hospitalization, or is a congenital anomaly, or important medical observation.
2. Associated with the use of the drug: there is a reasonable possibility that the experience may have been caused by the drug.
3. Unexpected adverse event: any adverse event that is not identified in nature, severity, or frequency in the current investigators brochure or package insert.
4. Grading: Toxicities and their standard grading, based on World Health Organization (WHO) criteria, are given in Appendix Ill. Adverse events which are not included in the WHO scale will be graded accordingly;
0=none
1=mild
2=moderate
3=severe
4=life threatening or debilitating
5=fatal
B. Reporting:
1. Adverse events will be reported as required by section 312.32 of the Code of Federal Regulations.
2. CellPath, Inc. will be provided with a copy of all serious adverse event reports filed with the FDA.

XIII. Statistical Considerations
A. All patients will be followed until disease progression or until death.
B. This is a pilot Phase II, non-randomized, single-armed study. The expected accrual rate is 5–6 patients per month. The duration of the study is anticipated to be 12 months; the duration of each subject's participation is likely to be twelve to eighteen months (the approximate duration of time to failure in ovarian cancer patients responding to agents known to be effective). Tumor measurements will be repeated on each patient at three to six week intervals.

C. A response probability of 20% would be of interest, while further testing would not be pursued if the response probability is 5% or lower. Initially, 14 patients will be entered. If at least one response is observed, an additional 11 patients will be entered. 5 or more responses out of 25 will be considered as evidence warranting further study of this regimen provided other factors, such as toxicity and survival also appear favorable. This design has a significance level (probability of falsely declaring an agent with a 5% response probability to warrant further study) of 5%, and a power (probability of correctly declaring an agent with a 20% response probability to warrant further study) of 94%.

| True Response Probability | 5% | 10% | 15% | 20% |
|---|---|---|---|---|
| Probability of stopping early | 36% | 12% | 4% | 1% |
| Probability of declaring agent warrants further study | 5% | 37% | 73% | 92% |

D. 25 patients are insufficient to estimate the probability of a particular toxicity to within ±0.16 (40 patients would be required for this).

However, any toxicity occurring with at least 10% probability is likely to be seen at least once (87% chance).

E. Kaplan-Meier survival statistics may be performed.

REFERENCE FOR EXAMPLE 6

1. Landis S et al. Cancer Statistics. Cancer J Clin 49:8–24, 1999.
2. McGuire W P, Hoskins W J, Brady M F et al. Cyclophosphamide and cisplatin compared with paclitaxel and cisplatin in patients with stage III and stage IV ovaraian cancer. N Engl J Med 334:1–6, 1996.
3. Ozols R F, Bundy B N, Fowler J et al. Randomized Phase III Study of Cisplatin (CIS/Paclitaxel (PAC) Versus Carboplatin ((CARBO)/PAC in Optimal Stage III Epthelial Ovarian Cancer (OC): A Gynecolog9ic Oncology Group Trial. (Proc ASCO Abstract 1373) J Clin Oncol 18:356a, 1999.
4. Repke KRH, Schon R, Megges R et al. Potential suitability of $Na^+/K^+$—transporting ATPase in pre-screens for anti-cancer agents. Anti-Cancer Drugs Design 10:177–187, 1995.
5. Hyun J-W, Shin J-E, Lim K-H et al. Evomonoside: The cytotoxic cardiac glycoside from Lepidium apetalum. Planta Med 61:294–295, 1995.
6. Inada A, Nakanishi T, Konoshima T, et al. Anti-tumor promoting activities of natural products. II. Inhibitory effects of digitoxin on two-stage carcinogenesis of mouse skin tumors and mouse pulmonary tumors. Biol. Pharm. Bull 16:930–931, 1993.
7. Stenkvist B, Bengtsson E, Eriksson O et al. Cardiac glycosides and breast cancer. Lancet Mar 10; 1(8115):563, 1979.
8. Stenkvist B, Bengtsson E, Eklund G et al. Evidence of a modifying influence of heart glucosides on the development of breast cancer. Analytical and Quantitative Cytology 2:49–54, 1980.
9. Stenkvist B, Bengtsson E, Dahlqvist B et al. Cardiac glycosides and breast cancer, revisited. N Engl J Med 306:484, 1982.
10. Goldin A G, Safa A R. Digitalis and Cancer. Lancet May 19; 1(8386):1134, 1984.
11. Friedman G D. Digitalis and Breast Cancer. Lancet Oct 13; 2(8407):875, 1984.
12. Stenkvist B. Is digitalis a therapy for breast carcinoma: Oncol Rep 6:493–496, 1999.
13. Gheorghiade M, Pitt B. Digitalis Investigation Group (DIG) trial: A stimulus for further research. Am Heart J 134:3–12, 1997.
14. Garg R, Gorlin R, Smith T et al. The effect of digoxin on mortality and morbidity inpatients with heart failure. N Engl J Med 336:525–533, 1997.

APPENDIX I

Performance Status: Patients will be graded according to the current Gynecology Oncology Group grading scale:

Grade Scale

0 Fully active; able to carry on all pre-disease activities without restriction.

1 Restricted in physically strenuous activity but ambulatory and able to carry out work of a light or sedentary nature, e.g., light housework, office work.

2 Ambulatory and capable of all self-care but unable to carry out any work activities. Up and about more than 50% of waking hours.

3 Capable of only limited self-care; confined to bed or chair more than 50% of waking hours.

4 Completely disabled. Cannot carry on any self-care. Totally confined to bed or chair.

5 Dead

It is to be understood that the invention is not to be limited to the exact details of operation, or to the exact compounds, compositions, methods, procedures or embodiments shown and described, as obvious modifications and equivalents will be apparent to one skilled in the art, and the invention is therefore to be limited only by the full scope of the appended claims.

APPENDIX I

Performance Status: Patients will be graded according to the current Gynecology Oncology Group grading scale:

Grade Scale

0 Fully active; able to carry on all pre-disease activities without restriction.

1 Restricted in physically strenuous activity but ambulatory and able to carry out work of a light or sedentary nature, e.g., light housework, office work.

2 Ambulatory and capable of all self-care but unable to carry out any work activities. Up and about more than 50% of waking hours.

3 Capable of only limited self-care; confined to bed or chair more than 50% of waking hours.

4 Completely disabled. Cannot carry on any self-care. Totally confined to bed or chair.

5 Dead

It is to be understood that the invention is not to be limited to the exact details of operation, or to the exact compounds, compositions, methods, procedures or embodiments shown and described, as obvious modifications and equivalents will be apparent to one skilled in the art, and the invention is therefore to be limited only by the full scope of the appended claims.

I claim:

1. A method for treating a susceptible neoplasm which comprises administering to a patient in need thereof an effective amount for treating the neoplasm of digitoxin or a pharmaceutical salt thereof, wherein said neoplasm is selected from the group consisting of mesotheliomas, sarcomas, and stromal cell tumors.

2. The method of claim 1 wherein the neoplasm is as carcoma, and wherein the sarcoma is selected from the group consisting of leiomyosarcomas, malignant fibrous histiocytoma, Ewing sarcoma, fibrosarcomas, chondrosarcomas, osteosarcomas, liposarcomas, rhabdomyo-sarcomas, hemangiocytomas, and myxosarcomas.

3. The method of claim 1 wherein the neoplasm is a mesothelioma, and wherein the mesothelioma is a lung mesothelioma.

4. The method of claim 1 wherein the neoplasm is a stromal cell tumor, and wherein the stromal cell tumor is selected from the group consisting of granulosa cell, thecoma, and Sertoli-Leydig tumors.

* * * * *

UNITED STATES PATENT AND TRADEMARK OFFICE
CERTIFICATE OF CORRECTION

PATENT NO. : 6,380,167 B1
DATED : April 30, 2002
INVENTOR(S) : Irwin Braude

It is certified that error appears in the above-identified patent and that said Letters Patent is hereby corrected as shown below:

<u>Column 25,</u>
Lines 5-10, should read:

-- 2. The method of claim 1 wherein the neoplasm is a sarcoma, and wherein the sarcoma is selected from the group consisting of leiomyosarcomas, malignant fibrous histiocytoma, Ewing sarcoma, fibrosarcomas, chondrosarcomas, osteosarcomas, liposarcomas, rhabdomyo-sarcomas, hemangiocytomas, and myxosarcomas.

Signed and Sealed this

Twenty-fourth Day of September, 2002

*Attest:*

*Attesting Officer*

JAMES E. ROGAN
*Director of the United States Patent and Trademark Office*